(12) United States Patent
Davies

(10) Patent No.: US 6,375,697 B2
(45) Date of Patent: Apr. 23, 2002

(54) APPARATUS AND METHOD FOR SCREENING PEOPLE AND ARTICLES TO DETECT AND/OR TO DECONTAMINATE WITH RESPECT TO CERTAIN SUBSTANCES

(75) Inventor: John H. Davies, Port Credit (CA)

(73) Assignee: Barringer Research Limited, Mississauga (CA)

(*) Notice: Subject to any disclaimer, the term of this patent is extended or adjusted under 35 U.S.C. 154(b) by 0 days.

(21) Appl. No.: 09/389,019

(22) Filed: Sep. 2, 1999

Related U.S. Application Data

(60) Provisional application No. 60/145,966, filed on Jul. 29, 1999.

(51) Int. Cl.⁷ .......................... B01D 35/14; B01D 53/34; G01N 1/22
(52) U.S. Cl. .......................... 55/340; 55/385.2; 55/467; 55/DIG. 34; 96/413; 96/417; 454/187; 454/230; 73/23.2
(58) Field of Search ....................... 55/339, 340, 385.2, 55/467, DIG. 34; 96/413, 417, FOR 166, FOR 170; 95/8, 273; 457/187, 230; 73/23.2, 863.41, 863.81

(56) References Cited

U.S. PATENT DOCUMENTS

| | | | | |
|---|---|---|---|---|
| 4,896,547 A | * | 1/1990 | Arney et al. | 73/863.81 |
| 4,987,767 A | * | 1/1991 | Corrigan et al. | 73/23.36 |
| 5,915,268 A | * | 6/1999 | Linker et al. | 73/23.2 |
| 6,073,499 A | * | 6/2000 | Settles | 73/864.81 |

* cited by examiner

*Primary Examiner*—Robert A. Hopkins
(74) *Attorney, Agent, or Firm*—Bereskin & Parr

(57) ABSTRACT

A walk-through portal or other enclosure is provided for at least one of detection of a predetermined substance on a subject and decontamination of a subject from a predetermined substance, the subject being either a person or, for other type of enclosure, an object, such as a suitcase. The walk-through portal defines an examination zone and can be substantially open on at least one side, to permit a subject readily to enter and to exit the examination zone. A closure closes off the examination zone from the exterior. An inlet into the examination zone and an outlet from the examination zone permit air or other gas to flow through it, and this is pumped by a pump, so as to entrain at least one of vapors and particulates from such substance. At least part of the exhaust through the outlet can be passed to an analyzer, such as an IMS, to detect substances of interest.

42 Claims, 2 Drawing Sheets

APPARATUS AND METHOD FOR SCREENING PEOPLE AND ARTICLES TO DETECT AND/OR TO DECONTAMINATE WITH RESPECT TO CERTAIN SUBSTANCES

This application claims the benefit of Ser. No. 60/145,966 filed Jul. 29, 1999.

FIELD OF THE INVENTION

This invention relates to both an apparatus for and method of screening people and articles, to detect exposure and/or to decontaminate with respect to substances of interest, particularly, toxic materials, such as chemical warfare gases and vapours and the like from industrial accidents.

BACKGROUND OF THE INVENTION

Rapid screening techniques are required to quickly identify people who may have been exposed to toxic emissions, notably either from chemical warfare gases and vapours or chemicals spilled or accidentally formed from industrial accidents. Often these substances are released or disseminated in liquid form, and the liquids have effectively low boiling points such that the vapours are readily emitted.

Following a chemical warfare agent attack, for example, numerous people could be contaminated, as for example in crowded metropolitan underground rail systems. Since nerve and chemical warfare agents are extremely toxic, quick response and remedial action is essential. If liquid agents were disseminated into closed areas, the contamination could be very high. Great care must therefore be taken to ensure that in a mixed population of victims or potential victims, those who are contaminated are quickly separated from those who are not. In the Tokyo Metropolitan Rail attack, sarin was used and the First Responders (i.e. emergency personnel such as Fire, Police or ambulance staff, who first arrived at the scene) were unable to separate contaminated from uncontaminated people. As a consequence, victims whose clothing had been contaminated with the sarin became sources of reliberation of the vapours, which then cross-contaminated people who were originally unaffected. Thus, the casualties from the attack were greatly multiplied. It is most desirable therefore to develop a quick screening system where individuals could pass through a walk-through portal, similar to Walk-Through Metal Detectors (WTMD) used in airports for screening passengers for concealed weapons. Just as WTMD systems detect the presence of metal objects, the inventor has realized that a similar screening system could be used to detect the presence of chemical agents. There is a need for easily deployed walk-through portal systems provided with air jets that can air brush people and speedily process possible victims on a walk-through basis.

SUMMARY OF THE INVENTION

The present invention is based on the realization that a curtain, using air or other gas, can quickly thermally desorb such high vapour pressure toxic materials which pass from the skin and/or clothing of the victims. The air is passed through a filtering clean up system to render it safe before re-emission. A pump is provided to draw air from the atmosphere, clean it before it is passed to blowers which direct air jets over the suspected victim(s) within the air portal device. To increase the efficiency of evaporation of toxic materials, the air flow may be preheated.

Such devices can be provided in a portable form such that they may be readily transported from site to site and quickly reassembled where chemical terrorism acts or industrial accidents may have occurred. Alternatively such portals can be permanently installed at critical sites.

The walk-through portal of the present invention can include a plenum which delivers a flow of high volume warm air at approximately 10,000 Litres/minute over the person under processing. The person walks into the portal and executes a 90° turn so that the air jets, preferably heated, can blow over the front and back areas of their body and sweeps the warm air exhaust stream into a collecting plenum. A simple portable breathing mask might be provided so that the subject will not inhale chemical agents liberated from their clothing and skin. The air collecting plenum, handling about 2,000 L per person, (i.e. based on a 12 second time period for each person in the portal) will exhaust the collected air through a high volume filtering system. The exhaust filter abstracts any desorbed chemicals from the air flow before it is exhausted to the open atmosphere.

Any liquid chemical agent on clothing is liberated and either passes as whole liquid or thickened agent droplets into the plenum for subsequent removal by the charcoal filtering system, or the agents are vaporized in situ into the air flow and also effectively removed by the same filter. If the chemical droplets have absorbed into clothing, the flow of the warm air flow will greatly assist in their liberation. Some agents which have low viscosity and high vapour pressure are thickened by adding inert material. This produces a very viscous material, which readily adheres to surfaces and evaporates slowly, a persistent agent which is more difficult to clean up.

An analytical instrument can be used to make chemical measurements on the air flow exhausted through the plenum prior to filtering. One such instrumental method is Ion Mobility Spectroscopy (IMS); a successful means for detecting and identifying CW agents. However, many other techniques exist. An enrichment process can allow agents to be removed from the high volume air flow so as to be transferred into a much lower air flow compatible with instruments such as an IMS detector. Other instruments can be used to monitor the effluent such as fast gas chromatographs, IR analyzers, electrochemical cells and other such devices according to their analytical capabilities and speed of response for the analytes of interest.

In actual operation, especially where large numbers of individuals may need to be processed, speed is of essence and a number of such prescreening warm air only portals could be provided. The preliminary processing involves basic air decontamination; the individuals could be subsequently screened through a second portal which incorporates the chemical measurement means to check if decontamination was successful. Where the number of victims are few, a single portal can perform the functions of decontamination and contamination monitoring.

The portals could be constructed as portable devices or "knock-down" kits, allowing for ease of transport and rapid assembly at the site of the chemical release. Evidently, such portals could be permanently constructed for us in chemical plants or military installations where dangerous chemical materials are stored, handled, processed or positioned. Additionally, such portals could be used as security screens at airport check points.

In accordance with a first aspect of the present invention, there is provided a walk-through portal for at least one of detection of a predetermined substance on a subject and decontamination of a subject from a predetermined substance, the walk-through portal comprising:

an enclosure defining an examination zone and being substantially open on at least one side, to permit a subject readily to enter and to exit the examination zone;

a closure means for substantially closing off the examination zone from the exterior;

an inlet into the examination zone and an outlet from the examination zone; and a pump for pumping a gas through the inlet into the examination zone, over a subject to entrain at least one of vapours and particulates from such substance, and out through the outlet.

The portal preferably includes at least one flexible screen, closing off the examination zone. More preferably, the walk-through portal is open on opposite sides thereof, to enable a subject to walk into the examination zone from one side and out from the examination through the other side, and the walk-through portal further includes flexible screens on both sides, closing off the examination zone.

Advantageously, the portal includes an output decontamination filter connected to the outlet from the examination zone, for ensuring that gas exhausted into the atmosphere is free from any contaminating substance and/or an inlet filter, mounted between the inlet and the examination zone, for filtering gas flowing into the examination zone.

Preferably, the walk-through portal includes an analyzer, connected to the outlet, for taking a sample of gas flowing through the outlet, whereby the analyzer determines the presence of said substance in the gas flowing through the outlet and/or a detection instrument connected to the inlet, for monitoring gas flowing into the examination zone for presence of contamination.

Instead of an open system, the portal can include a recirculation duct connected between the outlet and the inlet and a filter mounted in the recirculation duct, for cleaning gas exhausted from the examination zone of any contaminating substance, before the gas is recirculated back through the inlet into the examination zone.

In either version, the portal can include a supply of a decontamination agent, connected to the recirculation duct, downstream from the filter, for supply of a decontamination agent for one of neutralization, destabilizing and breaking down said substance.

An indicator can be connected to the analyzer and is operable to provide an indication as to whether a subject is or is not contaminated with said substance. A connection can be provided between the analyzer and the pump, for turning off the pump, after a predetermined period of time, when it is determined that said substance is not present, indicative that subject is not contaminated.

Another aspect of the present invention provides a device, for at least one of detection of a predetermined substance on an article and decontamination of an article from a predetermined substance, the device comprising:

an enclosure defining the examination zone, the enclosure being openable for insertion and removal of an article and being closable to close off the examination zone from the exterior;

an inlet into the examination zone and an outlet from the examination zone;

a pump for pumping a gas through the inlet into the examination zone, over the article to entrain at least one of vapours and particulates of said substance, and out through the outlet; and an analyzer connected to the outlet, for sampling gas flowing through the outlet, whereby the analyzer determines the presence of said substance, indicative of contamination of the article by said substance.

Yet another aspect of the present invention provides a method of effecting at least one of detection of a substance on a subject and decontamination of the subject, the method of comprising the steps of:

(1) enclosing the subject in an examination zone substantially closed off from the exterior;

(2) passing gas into the examination zone, to entrain at least one of vapours and particulates of said substance; and (3) withdrawing gas from the examination zone.

BRIEF DESCRIPTION OF THE DRAWING FIGURES

For a better understanding of the present invention and to show more clearly how it may be carried into effect, reference will now be made, by way of example to the accompanying drawings, in which.

DESCRIPTION OF THE PREFERRED EMBODIMENT

Figure 1:
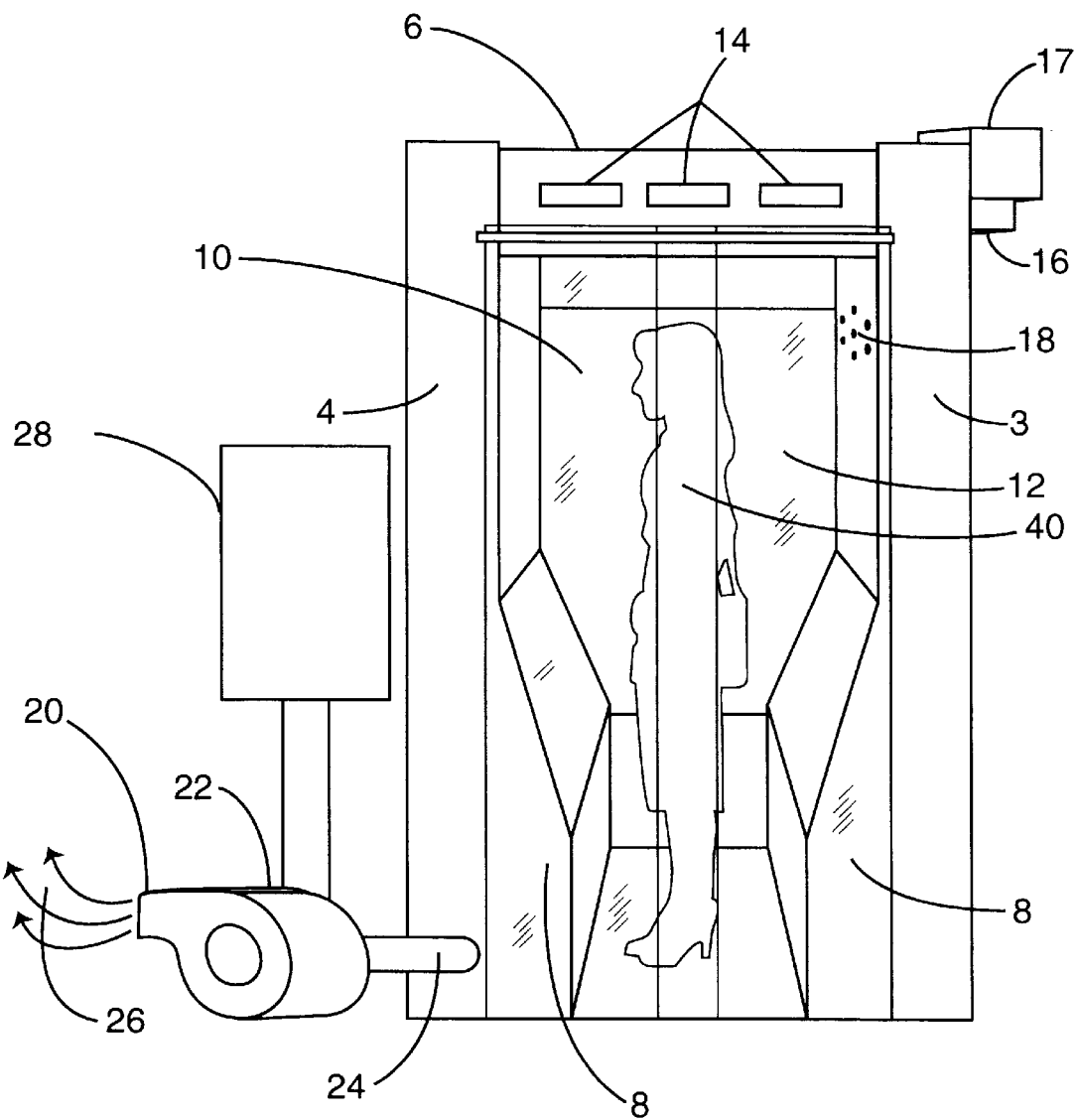
FIG. 1 is a walk-through portal in accordance with the present invention.

Referring first to FIG. 1, the apparatus of the present invention includes a main portal structure 2, which comprises two vertical side members 3,4 and a crosspiece 6 at the top. The vertical side members 3, 4 are generally vertical and parallel at the top thereof, and towards the bottom, include trapezoidal sections 8 shaped to match the human silhouette, ensuring efficient airflow and collection. The portal illustrated is one-sided, i.e. "walk-in" rather than "walk-through". The rear wall can have a solid portion below a window; either walk-in or walk-through versions are possible, but having a solid wall simplifies control of air flow and aids efficient sampling. Note that, in its broadest sense, the term "walk-through" is used in the claims to encompass a portal open on just one side and a portal open on both sides.

The vertical side members 3, 4 together with the crosspiece 6 define an examination zone 10. To close off this examination zone 10, flexible screens, indicated schematically at 12 are provided at the front and back of the apparatus, i.e. above and below the plane of FIG. 1.

In the crosspiece 6, inlets 14 are provided for ambient air. The inlets 14 are connected to a filter canister 16, which in turn is connected to a plurality of jet orifices 18. If desired, particularly for less volatile materials, a heater 17, downstream from filter 16, for preheating the air could be provided.

To draw air through the examination zone 10, a blower 20 is connected by an output decontamination filter 22 to an outlet 24, opening near the bottom of the examination zone 10. The orifices 18 are provided towards the top of the examination zone 10. It will be appreciated that for the blower or pump 20 to efficiently draw air through the examination zone 10, the flexible screens 12 must form a reasonably good seal with the exterior; on the other hand, slight leakage through the screens is not fatal and indeed serves to prevent leakage of any vaporized contaminants to the exterior. The exhaust stream from the blower 20 is indicated at 26.

To detect the presence of any particular substance of interest, a suitable analyzer 28 can be connected to the outlet 24, immediately upstream from the decontamination filter 22. Here, an ion mobility spectrometer is shown. Most analyzers would only take a small portion of the outlet flow, and this flow can be so small that the issue of filtering any output from the analyzer is not a concern. However, it would be advisable to filter this output, and this would be relatively simple.

Figure 2:
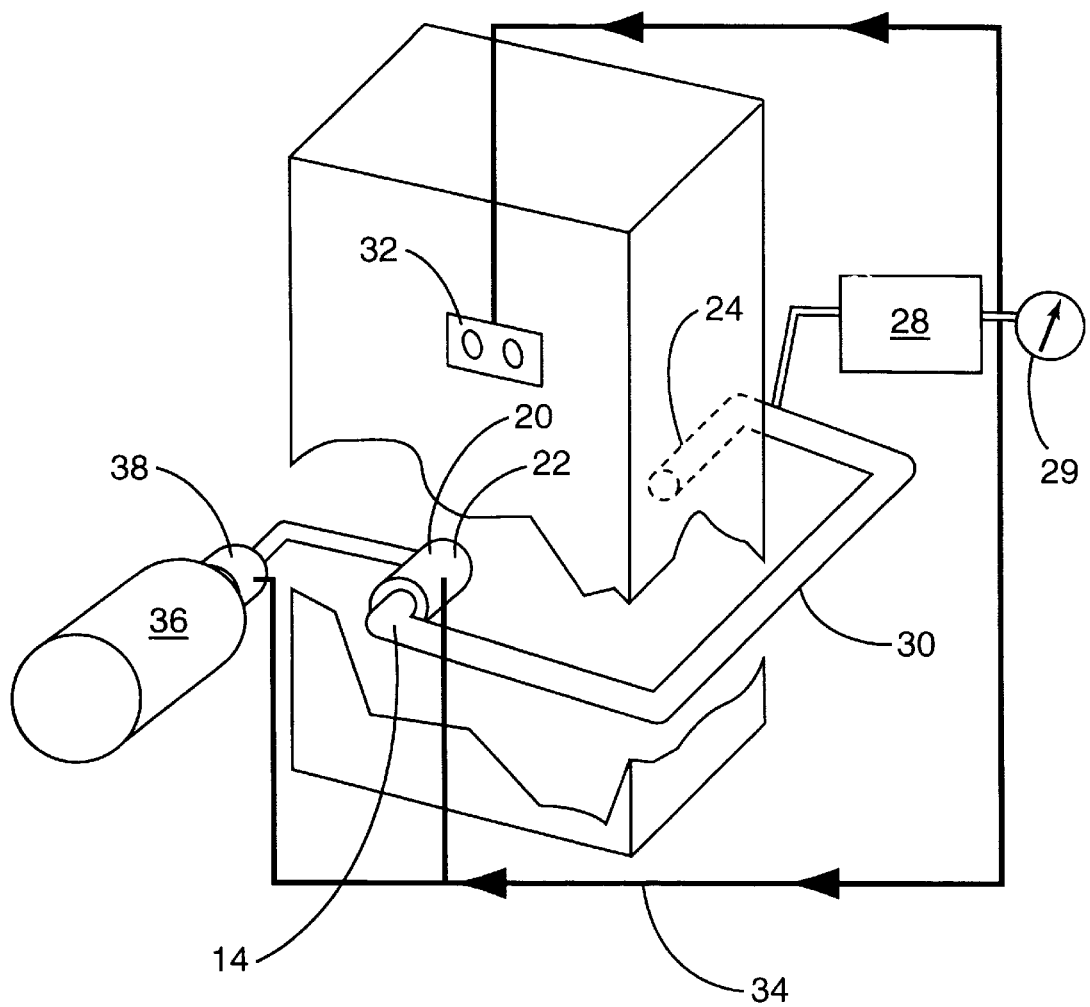
FIG. 2 shows schematically a perspective view of additional components of the walk-through portal of FIG. 1.

Turning to FIG. 2, this shows some optional, additional features for the apparatus or portal of the present invention. Here, the blower 20 and filter 22 are shown together, and the output of the blower 20 is connected to a recirculation duct or conduit 30. As the air has already been filtered through the output decontamination filter 22, the inlet filter canister 16 can be omitted and the recirculation duct 30 connected directly to the orifices 18 (detailed connections not shown). Note the blower 20, filter 22 are remote from the outlet 24 and are located close to the inlet (indicated schematically) in this embodiment.

FIG. 2 also shows that the analyzer or other output detector 28 can be provided with an indicator 29. Additionally, the output of the analyzer of the detector 28 can be connected to a warning indicator 32, for example a simple arrangement red/green warning lights to give either a warning or clear indication respectively. Further, a control signal can be connected to the blower 20, to stop the cycle when a clear signal is obtained, since further examination or detection is unnecessary, as indicated by connection 34.

A further optional variant of the invention is to provide a supply 36 of a decontamination agent, shown in FIG. 2, connected to the recirculation duct 30, where it is connected to the inlet 14 of the main portal structure. A valve 38 could be provided between the supply 34 and the duct 30, the valve 38 being connected to the output of the analyzer 28. The arrangement is such that when a particular substance is detected, then the valve 38 is open, to effect decontamination of the person within the main portal structure 2.

As detailed below, the walk-through portal of the present invention can be configured for different applications, either fixed or permanent. For a portable installation, the portal should be constructed of lightweight materials, such as plastics, which render easy transportation, and quick strip-down and reassembly, thereby facilitating movement to different sites. The flexible screens 12 could be simple plastic strips or sheets, which are preferably easily removable for decontamination. For a simple installation, screens, or a screen, could be provided on just one side, although this would require a person to enter and exit from the same side.

In use, a person or suspect target, indicated at 40, enters the portal by walking through flexible screens 12. If a person has bags or luggage, these can be checked with the individual, if small, or subject to a separate check. Once the person 40 is in the examination zone 10, the flexible screens 12 effectively, efficiently and quickly seal the zone 10. The blower 20 is then activated and the outside ambient air is drawn into the portal through the inlet 14 and filtered through the filter canister 16, which can comprise charcoal or like material. The air is then heated by the heater 17, if desired, and is drawn into the interior volume, or examination zone 10 through the series of jet orifices 18.

The air pressure and flow are sufficient to levitate solid particles off the subject 40 and/or provide sufficient heat input to the toxic materials resident on the surface of the subject or victim 40 and his/her clothing, to cause their evaporation into the exhaust flow. The exhaust flow is drawn through the outlet duct 24 and decontamination filter 22 by the blower 20. Both filters 16, 22 have sufficient volumetric capacity of absorbent materials, such as activated charcoal or the like, to ensure sufficient filtering action for the intended duration of decontamination operation, and the likely number of victims to be processed. The canisters can be made to be easily removable and rechargeable or indeed discardable.

Several applications are contemplated for the walk-through portal of the present invention, including:

Transportable Decontamination Portals for First Responders and other emergency response teams. These units would be configured to be quickly set up. In cases of terrorist attacks and chemical toxic releases, the fastest possible response to provide decontamination and provision of uncontaminated air flow is vital.

Fixed Portal systems could be permanently established in key facilities or in areas where dangerous and volatile chemicals are stored, handled and analyzed, e.g. major manufacturing installations and the like.

Prescreening Portals. These could be fixed; but it is expected that this variant is best suited to the transportable portal. A prescreening or warm air portal could be provided to decontaminate people, who would then be checked, to ensure this was successful in a regular portal. A prescreening portal would omit the analyzer 28 and associated indication elements, but usually would include the heater 17.

A portion of the flow from the outlet duct 24 is branched off into the analyzer 28. It can be noted that an advantage of having the blower as the last element in the flow path is that the rest of the device is operating at a sub-atmospheric pressure. Hence, if there are any leaks, this will merely tend to draw additional ambient air into the system. In contrast, if the blower was put anywhere upstream, then portions of the flow path downstream from the blower 20 would be above atmospheric pressure, so that any leaks may result in leakage of heated air with high levels of toxic materials present. Although not shown, the analyzer 28 would have its own suction system. More preferably, given current analyzer technology, the exhaust flow would be passed through a pre-concentrator, which would absorb the agent. Periodically, the main flow would by-pass the pre-concentrator, which would be rapidly heated, and a small sampling flow used to collect the desorbed agent and transfer it to the analyzer.

In use, the analyzer 28 is monitored, to check for presence of materials of interest on the subject or person 40 within the examination zone 10. If no such substance is detected within a predetermined or set time, then the examination is ended, the blower 20 is turned off and the person 40 is told that they can pass out of the device or unit. A new subject or person 40 is then processed through the device of the invention.

Where the variant of FIG. 2 is used, then this operates in the same manner as the version of FIG. 1. The indication provided at 32 can either be mounted so as to be visible just to an operator and/or visible to the person undergoing the test. In either case, if a clear indication is given, then as above, the person 40 is told to exit the device. If a warning is given, then appropriate action is taken. For example, in the case of chemical contamination, the person would immediately be subject to appropriate decontamination procedures. On the other hand, if the detection was of, for example, drugs or explosives at a border crossing, then the person 40 would be taken away for further examination and questioning.

For decontamination uses, as mentioned, a supply of decontamination agent 36 can be provided. Where this is present, it would typically by charged with suitable decontamination agent to deal with one particular chemical known to have been spilt. When this chemical is detected, then the supply 36 is activated, to decontaminate the person 40 in the examination zone 10, who the device indicates is contaminated. As noted above, this can either be automatic, where a suitable valve is present, or it can be effected manually. The agent from the supply 36 can be such as to either break down, neutralize or destabilize the toxic chemical or concern.

It is to be appreciated that the use of the analyzer 28 is optional. For applications, where a chemical has been spilt, and it is believed that victims may have been exposed to it, it may be known that simple flushing with heated air will remove the chemical. In such cases, it is sufficient to process each person for a sufficient length of time through the device of the present invention, without necessarily running any check or analysis for the substance of concern. However, in these cases, some form of analyzer is desirable to give a level of confidence that safety has been achieved. Also, the presence of an analyzer enables the progress of decontamination to be assessed and the duration of the treatment to be adjusted, or in extreme cases, taking other measures to decontaminate an individual.

The apparatus can also include some detector or instrument at the inlet (indicated schematically), or an equivalent location in FIG. 2, to ensure that the incoming air is sufficiently clean prior to use. For this purpose, it may be possible to use the analyzer or detector 28, which could be provided with alternative, switchable connections, for sampling either air flowing into the decontamination zone 10, or air leaving the decontamination zone 10.

The invention has been described utilizing ambient air as the gas flowing through the decontamination zone. This is practical for most applications, and provides a high volume of gas, without requiring any external supply. However, it will be appreciated that, for some specialized applications, e.g. examining small packages and the like, it may be desirable to provide a separate source of clean, dry gas.

In the case of chemical warfare agent detection, instruments such as ion mobility spectrometers can be used to detect chemical warfare agents such as VX (o-ethyl-S-(2-isopropylaminoethyl) methyl phosphonthiolate), GA (ethyl N, N-dimethylphosphoramidocyanidate), GB (Isopropyl methylphosphonofluoridate), GD (Phosphonofluoridic acid, methyl-,1,2,2-trimethylpropyl ester), L (Dichloro-(2-chlorovinyl) arsine), and H (BIS-(2-chloroethyl) sulfide). Other analytical instruments can be used dependent upon the analyte, and the above description is in no way intended as a limitation as to the means or instrumental method of detection.

While the above description particularly describes a walk-through air portal for decontamination of liquid chemical agents and industrial toxic liquid chemicals, it can be appreciated that decontamination can be achieved for particulate and solid material, radioactive/nuclear dust and debris and even explosives and drug particles.

It is, for example known that a significant decomposition breakdown product of cocaine is ecgonidinemethylester (EDME), which is significantly more volatile than cocaine. Thus, the method here described can be used to liberate EDME as an indicator of cocaine concealed on travellers or suspects thought to be concealing cocaine. Travellers could be passed through such an air portal at border crossings to assist customs officers in searching for contraband. Instrumental means such as Gas Chromatography (GC), Ion Mobility Spectrometers (IMS) or GC/IMS are well established techniques able to detect cocaine either as particulate, or vapour, or the EDME vapour itself. The appropriate selection of the instrumental detector depends upon threshold sensitivities achieved, false alarm rates, throughputs, speed of response, costs and ease of use.

It will also be recognized that while the foregoing descriptions relate to a process for decontaminating people, the device and method of the present invention are applicable to the decontamination of equipment, stores, military items and the like, which may be placed either within the portals or within fixed or portable chambers more suitably adapted to this specific purpose.

In a more sophisticated version of the system a laser can monitor the height of the individuals to activate the most appropriate jet orifices 18, to maximize the impact of air jets on the body of the person being decontaminated. This enables a person's size to be taken into account. It may require, for example, valves controlling connections to the jet orifices 18.

If adequate sensitivity is available to the analytical instruments very low levels of contamination can be detected. The miosis levels which are generated by longer term continuous exposure to low levels of chemical concentration can thereby be assessed. Military personnel can be monitored periodically, even daily after military missions, by portable portals which provide a decontamination and miosis check.

While the description of the preferred embodiment has focused on toxic chemicals and chemical warfare agents, it must be recognized that it is not limited to this set of applications but can be more widely used as a security prescreening device or monitor as in airport security. It could be interfaced to walk-through metal detectors to provide a combined anti-terrorist security device for weapons and chemical attack agents, and this is another example of a fixed installation.

A further aspect of the present invention is to configure the device as an inspection chamber constructed to monitor luggage, baggage and cargo, which would be individually placed within it or moved through conveyors, as in conventional x-ray inspection systems. Such inspection systems can be used as screening stations for detection of toxic chemicals, improvised chemical weapons or prohibited chemical substances.

What is claimed is:

1. A walk-through portal for at least one of detection of a predetermined substance on a subject and decontamination of a subject from a predetermined substance, the walk-through portal comprising:
    an enclosure defining an examination zone and being substantially open on at least one side, to permit a subject readily to enter and to exit the examination zone;
    a closure means for substantially closing off the examination zone from the exterior;
    an inlet into the examination zone and an outlet from the examination zone;
    a pump for pumping a gas through the inlet into the examination zone, over a subject to entrain at least one of vapours and particulates from such substance, and out through the outlet; and
    at least one flexible screen, closing off the examination zone.

2. A walk-through portal as claimed in claim 1, which is open on opposite sides thereof, to enable a subject to walk into the examination zone from one side and out from the examination through the other side, wherein the walk-through portal further includes flexible screens on both sides, closing off the examination zone.

3. A walk-through portal as claimed in claim 1, which includes an output decontamination filter connected to the outlet from the examination zone, for ensuring that gas exhausted into the atmosphere is free from any contaminating substance.

4. A walk-through portal as claimed in claim 3, which includes an inlet filter, mounted between the inlet and the examination zone, for filtering gas flowing into the examination zone.

5. A walk-through portal as claimed in claim 4, which includes an analyzer, connected to the outlet, for taking a sample of gas flowing through the outlet, whereby the analyzer determines the presence of said substance in the gas flowing through the outlet.

6. A walk-through portal as claimed in claim 5, which includes a detection instrument connected to the inlet, for monitoring gas flowing into the examination zone for presence of contamination.

7. A walk-through portal as claimed in claim 1, which includes a recirculation duct connected between the outlet and the inlet and a filter mounted in the recirculation duct, for cleaning gas exhausted from the examination zone of any contaminating substance, before the gas is recirculated back through the inlet into the examination zone.

8. A walk-through portal as claimed in claim 7, which includes an analyzer connected to the recirculation duct, for taking a sample of the gas flow exhausted from the examination zone, upstream from the filter, whereby the analyzer can determine the presence of said substance in the exhausted gas flow.

9. A walk-through portal as claimed in claim 8, which includes a detection instrument, connected into the recirculation duct downstream from the filter, for ensuring that gas recirculated into the examination zone is free from contamination.

10. A walk-through portal as claimed in claim 8, which includes a supply of a decontamination agent, connected to the recirculation duct, downstream from the filter, for supply of a decontamination agent for one of neutralization, destabilizing and breaking down said substance.

11. A walk-through portal as claimed in claim 5 or 8, which includes an indicator connected to the analyzer and operable to provide an indication as to whether a subject is or is not contaminated with said substance.

12. A walk-through portal as claimed in claim 5 or 8, which includes a connection between the analyzer and the pump, for turning off the pump, after a predetermined period of time, when it is determined that said substance is not present, indicative that the subject is not contaminated.

13. A walk-through portal as claimed in claim 5 or 8, which includes a heater mounted upstream of the inlet for heating gas flowing to the inlet.

14. A walk-through portal for at least one of detection of a predetermined substance on a subject and decontamination of a subject from a predetermined substance, the walk-through portal comprising:
 an enclosure defining an examination zone and being substantially open on at least one side, to permit a subject readily to enter and to exit the examination zone;
 a closure means for substantially closing off the examination zone from the exterior;
 an inlet into the examination zone and an outlet from the examination zone;
 a pump for pumping a gas through the inlet into the examination zone, over a subject to entrain at least one of vapours and particulates from such substance, and out through the outlet; and
 a detection instrument connected to the inlet, for monitoring gas flowing into the examination zone for presence of contamination.

15. A walk-through portal as claimed in claim 14, which includes at least one flexible screen, closing off the examination zone.

16. A walk-through portal as claimed in claim 15, which is open on opposite sides thereof, to enable a subject to walk into the examination zone from one side and out from the examination through the other side, wherein the walk-through portal further includes flexible screens on both sides, closing off the examination zone.

17. A walk-through portal as claimed in claim 14, which includes an output decontamination filter connected to the outlet from the examination zone, for ensuring that gas exhausted into the atmosphere is free from any contaminating substance.

18. A walk-through portal as claimed in claim 17, which includes an, inlet filter, mounted between the inlet and the examination zone, for filtering gas flowing into the examination zone.

19. A walk-through portal as claimed in claim 18, which includes an analyzer, connected to the outlet, for taking a sample of gas flowing through the outlet, whereby the analyzer determines the presence of said substance in the gas flowing through the outlet.

20. A walk-through portal as claimed in claim 14, which includes a recirculation duct connected between the outlet and the inlet and a filter mounted in the recirculation duct, for cleaning gas exhausted from the examination zone of any contaminating substance, before the gas is recirculated back through the inlet into the examination zone.

21. A walk-through portal as claimed in claim 20, which includes an analyzer connected to the recirculation duct, for taking a sample of the gas flow exhausted from the examination zone, upstream from the filter, whereby the analyzer can determine the presence of said substance in the exhausted gas flow.

22. A walk-through portal as claimed in claim 21, which includes a detection instrument, connected into the recirculation duct downstream from the filter, for ensuring that gas recirculated into the examination zone is free from contamination.

23. A walk-through portal as claimed in claim 21, which includes a supply of a decontamination agent, connected to the recirculation duct, downstream from the filter, for supply of a decontamination agent for one of neutralization, destabilizing and breaking down said substance.

24. A walk-through portal as claimed in claim 19 or 21, which includes an indicator connected to the analyzer and operable to provide an indication as to whether a subject is or is not contaminated with said substance.

25. A walk-through portal as claimed in claim 19 or 21, which includes a connection between the analyzer and the pump, for turning off the pump, after a predetermined period of time, when it is determined that said substance is not present, indicative that the subject is not contaminated.

26. A walk-through portal as claimed in claim 19 or 21, which includes a heater mounted upstream of the inlet for heating gas flowing to the inlet.

27. A walk-through portal for at least one of detection of a predetermined substance on a subject and decontamination of a subject from a predetermined substance, the walk-through portal comprising:

an enclosure defining an examination zone and being substantially open on at least one side, to permit a subject readily to enter and to exit the examination zone;

a closure means for substantially closing off the examination zone from the exterior;

an inlet into the examination zone and an outlet from the examination zone;

a pump for pumping a gas through the inlet into the examination zone, over a subject to entrain at least one of vapours and particulates from such substance, and out through the outlet;

a recirculation duct connected between the outlet and the inlet;

a filter mounted in the recirculation duct for cleaning gas exhausted from the examination zone of any contaminating substance before the gas is recirculated back through the inlet into the examination zone; and a supply of a decontamination agent, connected to the recirculation duct, downstream from the filter, for supply of a decontamination agent for one of neutralization, destabilizing and breaking down said substance.

28. A walk-through portal as claimed in claim 27, which includes at least one flexible screen, closing off the examination zone.

29. A walk-through portal as claimed in claim 28, which is open on opposite sides thereof, to enable a subject to walk into the examination zone from one side and out from the examination through the other side, wherein the walk-through portal further includes flexible screens on both sides, closing off the examination zone.

30. A walk-through portal as claimed in claim 27, which includes an output decontamination filter connected to the outlet from the examination zone, for ensuring that gas exhausted into the atmosphere is free from any contaminating substance.

31. A walk-through portal as claimed in claim 30, which includes an inlet filter, mounted between the inlet and the examination zone, for filtering gas flowing into the examination zone.

32. A walk-through portal as claimed in claim 31, which includes an analyzer, connected to the outlet, for taking a sample of gas flowing through the outlet, whereby the analyzer determines the presence of said substance in the gas flowing through the outlet.

33. A walk-through portal as claimed in claim 32, which includes a detection instrument connected to the inlet, for monitoring gas flowing into the examination zone for presence of contamination.

34. A walk-through portal as claimed in claim 22, which includes an analyzer connected to the recirculation duct, for taking a sample of the gas flow exhausted from the examination zone, upstream from the filter, whereby the analyzer can determine the presence of said substance in the exhausted gas flow.

35. A walk-through portal as claimed in claim 34, which includes a detection instrument, connected into the recirculation duct downstream from the filter, for ensuring that gas recirculated into the examination zone is free from contamination.

36. A walk-through portal as claimed in claim 32 or 34, which includes an indicator connected to the analyzer and operable to provide an indication as to whether a subject is or is not contaminated with said substance.

37. A walk-through portal as claimed in claim 32 or 34, which includes a connection between the analyzer and the pump, for turning off the pump, after a predetermined period of time, when it is determined that said substance is not present, indicative that the subject is not contaminated.

38. A walk-through portal as claimed in claim 32 or 34, which includes a heater mounted upstream of the inlet for heating gas flowing to the inlet.

39. A device, for at least one of detection of a predetermined substance on an article and decontamination of an article from a predetermined substance, the device comprising:

an enclosure defining the examination zone, the enclosure being openable for insertion and removal of an article and being closable to close off the examination zone from the exterior;

an inlet into the examination zone and an outlet from the examination zone;

a pump for pumping a gas through the inlet into the examination zone, over the article to entrain at least one of vapours and particulates of said substance, and out through the outlet;

an analyzer connected to the outlet, for sampling gas flowing through the outlet, whereby the analyzer determines the presence of said substance, indicative of contamination of the article by said substance;

a recirculation duct connected between the inlet and the outlet; and a supply of decontamination agent, connected to the recirculation duct, for entrainment into gas flow into the examination zone for decontaminating an article when said substance is detected.

40. A device as claimed in 39, which includes a single filter for filtering gas prior to entry into the examination zone.

41. A device as claimed in claims 39 or 40, which includes at least one of an output decontamination filter connected to the outlet, and an inlet filter connected to the inlet.

42. A device as claimed in claims 39 or 40, which includes an indicator means, connected to the analyzer, for providing an indication of the presence of the predetermined substance.

* * * * *